United States Patent
Pogue et al.

(10) Patent No.: US 10,201,718 B2
(45) Date of Patent: Feb. 12, 2019

(54) METHOD AND SYSTEM FOR USING CHERENKOV RADIATION TO MONITOR BEAM PROFILES AND RADIATION THERAPY

(75) Inventors: Brian William Pogue, Hanover, NH (US); David Joseph Gladstone, Norwich, VT (US); Scott Christian Davis, Woodsville, NH (US); Johan Jakob Axelsoon, Lund (SE); Adam Kenneth Glaser, Lebanon, NH (US); Rongxiao Zhang, Norwich, VT (US)

(73) Assignee: THE TRUSTEES OF DARTMOUTH COLLEGE, Hanover, NH (US)

( * ) Notice: Subject to any disclaimer, the term of this patent is extended or adjusted under 35 U.S.C. 154(b) by 441 days.

(21) Appl. No.: 14/118,825

(22) PCT Filed: May 18, 2012

(86) PCT No.: PCT/US2012/038609
§ 371 (c)(1),
(2), (4) Date: Nov. 19, 2013

(87) PCT Pub. No.: WO2012/159043
PCT Pub. Date: Nov. 22, 2012

(65) Prior Publication Data
US 2014/0114150 A1    Apr. 24, 2014

Related U.S. Application Data

(60) Provisional application No. 61/488,129, filed on May 19, 2011, provisional application No. 61/585,366, filed on Jan. 11, 2012.

(51) Int. Cl.
*A61B 5/05* (2006.01)
*A61B 5/00* (2006.01)
(Continued)

(52) U.S. Cl.
CPC .......... *A61N 5/1065* (2013.01); *A61B 5/0071* (2013.01); *A61B 5/1455* (2013.01);
(Continued)

(58) Field of Classification Search
None
See application file for complete search history.

(56) References Cited

U.S. PATENT DOCUMENTS 4,215,274 A * 7/1980 Segall ..................... G01T 1/22
                                                    250/361 R
5,117,829 A     6/1992 Miller et al.
(Continued)

FOREIGN PATENT DOCUMENTS

GB         681050 A  * 10/1952  .......... G03B 42/025
WO    2011005862 A2     1/2011
(Continued)

OTHER PUBLICATIONS

"Cho et al.," "Cerenkov radiation imaging as a method for quantitative measurements of beta particles in a microfluidic chip," Phys Med Biol. Nov. 21, 2009; 54 (22): 6757-6771.*
(Continued)

*Primary Examiner* — Patricia J Park
(74) *Attorney, Agent, or Firm* — Lathrop Gage LLP

(57) ABSTRACT

A system for providing monitored radiation therapy has a high energy radiation source, apparatus for excluding uncontrolled ambient light, and apparatus for collecting light emitted from a subject. The system has apparatus for spectrally analyzing the collected light, and a processor for determining oxygenation or other metabolic function of tissue within the subject from spectral analysis of the collected light. The system monitors radiation therapy by providing a beam of high energy radiation; collecting Cherenkov and/or photoluminescent light from the subject,
(Continued)

the light generated along the beam; spectrally analyzing the light; and determining oxygenation or metabolic function of tissue from the spectral analysis. Beam profile of the system is calibrated by imaging from multiple angles Cherenkov and/or photoluminescent light emitted by a phantom placed in the beam in lieu of a subject, captured images are analyzed to determine beam profile.

20 Claims, 8 Drawing Sheets

(51) Int. Cl.
    *A61N 5/10*     (2006.01)
    *A61B 5/1455*   (2006.01)
    *G01T 1/22*     (2006.01)
(52) U.S. Cl.
    CPC .............. *A61N 5/1075* (2013.01); *G01T 1/22* (2013.01); *A61N 2005/1076* (2013.01)

(56) References Cited

U.S. PATENT DOCUMENTS

| | | | |
|---|---|---|---|
| 6,123,719 A | 9/2000 | Masychev | |
| 6,518,580 B1* | 2/2003 | van Bibber | G01T 1/22 250/397 |
| 6,552,347 B1 | 4/2003 | Dimcovski | |
| 2003/0143637 A1* | 7/2003 | Selvan | G01N 21/07 506/9 |
| 2003/0225325 A1 | 12/2003 | Kagermeier et al. | |
| 2006/0215885 A1* | 9/2006 | Kates | A01M 31/002 382/120 |
| 2006/0285639 A1 | 12/2006 | Olivera et al. | |
| 2007/0164225 A1* | 7/2007 | Pang | G01T 1/22 250/367 |
| 2009/0018415 A1* | 1/2009 | Robinson | A61B 5/14558 600/310 |
| 2010/0119032 A1 | 5/2010 | Yan et al. | |
| 2010/0145416 A1* | 6/2010 | Kang | A61B 5/0059 607/89 |
| 2010/0254586 A1 | 10/2010 | Fanenbruck | |
| 2010/0330545 A1* | 12/2010 | Tian | A61B 17/00 434/267 |
| 2010/0331927 A1 | 12/2010 | Cottrell et al. | |
| 2011/0001049 A1 | 1/2011 | Shibuya | |
| 2011/0117025 A1* | 5/2011 | Dacosta | A61B 5/0059 424/9.6 |
| 2011/0163236 A1* | 7/2011 | Arodzero | G01V 5/0008 250/361 R |
| 2012/0220870 A1* | 8/2012 | Gambhir | A61K 49/0013 600/431 |
| 2012/0276002 A1* | 11/2012 | Yoo | A61K 49/0002 424/1.49 |
| 2013/0044185 A1 | 2/2013 | Krishnaswamy et al. | |
| 2013/0102879 A1 | 4/2013 | Maclaren et al. | |
| 2013/0108132 A1* | 5/2013 | Klose | A61B 5/0073 382/131 |
| 2013/0188856 A1 | 7/2013 | Adler, Jr. et al. | |
| 2013/0259339 A1* | 10/2013 | Tian | G06T 11/003 382/131 |
| 2014/0064554 A1 | 3/2014 | Coulter et al. | |
| 2014/0114150 A1 | 4/2014 | Pogue et al. | |

FOREIGN PATENT DOCUMENTS

| | | |
|---|---|---|
| WO | 2012159043 A2 | 11/2012 |
| WO | WO 2014/020360 | 2/2014 |

OTHER PUBLICATIONS

PCT Patent Application PCT/US12/38609 International Search Report and Written Opinion dated Dec. 3, 2012, 11 pages.
PCT Patent Application PCT/US2014/066668 International Search Report and Written Opinion dated Feb. 24, 2015, 11 pages.
Fodor et al. (2016), "Aesthetic Applications of Intense Pulsed Light", Springer-Verlag London Limited 2011, DOI: 10.1007/978-1-84996-456-2_2.
Jarvis et al. (2014), "Cherenkov Video Imaging Allows for the First Visualization of Radiation Therapy in Real Time", Int J Radiation Oncol Biol Phys, pp. 1-8.
International Search Report and Written Opinion dated Jul. 27, 2016 for International Application No. PCT/US2016/029458.
International Preliminary Report on Patentability dated May 24, 2016, for International Application No. PCT/US2014/066668.

\* cited by examiner

METHOD AND SYSTEM FOR USING CHERENKOV RADIATION TO MONITOR BEAM PROFILES AND RADIATION THERAPY

RELATED APPLICATIONS

The present document claims priority from U.S. Provisional Patent Application 61/488,129 filed 19 May 2011, and from U.S. Provisional Patent Application 61/585,366 filed 11 Jan. 2012; the disclosures of which are hereby incorporated by reference.

GOVERNMENT INTEREST

This invention was made with government support under grant nos. R01 CA120368; , R01 CA109558, and R21 EB179959 awarded by the National Institutes of Health. The government has certain rights in the invention.

FIELD

The present document describes apparatus and methods for monitoring and controlling radiation treatments such as are frequently administered in malignant diseases.

BACKGROUND

It is desirable when treating cancers with radiation to have a high ratio of energy deposited in the tumor, relative to energy deposited in normal tissues surrounding the tumor, resulting in a high therapeutic ratio of tumor to normal dose. Radiation treatments using high energy electron or particle beams and high energy photon beams are used in the treatment of some cancers because these provide the higher tumor to normal surrounding tissue dose ratio with deeper penetration, relative to lower energy or x-ray beams. Such beams are typically provided by a linear accelerator, by a cyclotron, or related apparatus.

Charged particles, such us electrons, positrons, protons, or alpha particles, moving at greater than the effective speed of light in a medium tend to slow down while releasing Cherenkov radiation. Mammalian tissue, including human tissue, is a medium where the speed of light is reduced relative to air or vacuum due to its refractive index being greater than unity. Therefore fast-moving charged particles release Cherenkov radiation after entering such tissue. Water is also a medium where the speed of light is reduced relative to air or vacuum, fast-moving charged particles in water also release Cherenkov radiation after entering such water. Cherenkov emission has been detected with incident radiation in the range of 6 to 24 MeV energies for electrons, and for gamma-ray photons of 6 to 18 MV which Compton scatter to produce energetic electrons which in turn produce Cherenkov radiation. Since the threshold for emitting Cherenkov depends on velocity, and energy depends on both velocity and mass, Cherenkov radiation will be released from beams of protons and other charged particles at significantly higher energies.

When this Cherenkov light is induced in tissue, it is predominantly blue in color, but with a broad spectrum which tapers off into the green, red, and NIR with an inverse square wavelength dependence given by the Frank-Tamm formula. This light emitted in tissue is attenuated by absorbers in the tissue, and can also excite other molecular species in tissue, inducing their photo-luminescence (fluorescence or phosphorescence).

Prior to treating patients with particle beams, it is desirable to know the shape of the beam, and to verify that the beam shape is as planned. Additionally, when beams enter tissue it is important to accurately predict how radiation beam shape varies with depth in tissue, to ensure adequate dosage to tumor while minimizing dosage to surrounding normal tissues. If beam shape and position is adjusted by positioning deflection magnets or shielding devices, it can be important to confirm that the resulting beam shape and dosage profile are as desired prior to exposing patients to the beam; radiation treatment centers may therefore desire to confirm beam shape and dose profile for complex beam shaping procedures for each patient, or as part of routine calibration and maintenance.

Manufacturers of radiation treatment devices often prepare documentation of beam shapes and dosage profiles produced by common configurations of their devices for training users and guiding operators in using their machines to treat patients. Further, they must seek regulatory approvals of their machines, and as part of the regulatory approvals process they are expected to provide documentation of beam shapes and dosage profiles achievable by their machines. Manufacturers may therefore need to accurately verify and document beam profiles for this regulatory approval process.

SUMMARY

A system for providing monitored radiation therapy has a high energy radiation source, apparatus for excluding uncontrolled ambient light, and apparatus for collecting light emitted from a subject. The system has apparatus for spectrally analyzing the collected light, and a processor for determining oxygenation or other metabolic function of tissue within the subject from spectral analysis of the collected light. The system monitors radiation therapy by providing a beam of high energy radiation; collecting Cherenkov and/or fluorescent light from the subject, the light generated along the beam; spectrally analyzing the light; and determining oxygenation or metabolic function of tissue from the spectral analysis. Beam profile of the system is calibrated by imaging from multiple angles Cherenkov and/or fluorescent light emitted by a phantom placed in the beam in lieu of a subject; captured images are analyzed to determine the beam profile. In embodiments, the system spectrally analyzes the collected light, and a processor determines hemoglobin oxygen saturation of tissue within the subject from spectral analysis of light collected from the subject. The emitted light can also be used to quantify endogenous or exogenously administered fluorescent or phosphorescent species in the tissue, which can be indicators of other tissue properties such as receptor density, oxygenation, and metabolic function.

In an embodiment, a system for providing and monitoring radiation therapy has a source of high energy radiation disposed to provide a radiation beam to a treatment zone; apparatus for preventing interference by room lighting; apparatus for collecting light from the treatment zone; a detector for detecting the collected light; a processor adapted to determine an oxygenation of tissue within a subject in the treatment zone from detected light.

A method of monitoring radiation therapy of a subject includes steps of providing a beam of high energy radiation for radiation therapy, the high energy radiation of at least 6 MeV for electrons and photons; collecting light emitted from the subject, the light emitted as Cherenkov radiation generated along the beam; spectrally analyzing the collected light; and determining an oxygenation of tissue within the subject from the spectral analysis of light collected from the subject.

In an embodiment, a system provides a radiation beam for radiation therapy and is adapted to document radiation beam profile, the system including: a tissue phantom containing a substantially transparent or translucent material positionable in the treatment zone and having an index of refraction greater than that of vacuum, or a tissue equivalent scintillating material; a source of high energy radiation capable of providing a beam of radiation, the radiation having sufficient energy to induce Cherenkov radiation in the phantom; one or more cameras positioned to image an emissions zone in an intersection of the beam and the phantom; the one or more cameras adapted to capture a plurality of images of the emissions zone from a plurality of angles; and an image processing system comprising apparatus for receiving images from the one or more cameras, at least one processor, and a memory having machine readable instructions for processing the images from the one or more cameras to construct a tomographic three-dimensional model of the emissions zone. In a particular embodiment, a fluorescent material is present in the phantom.

DETAILED DESCRIPTION OF THE EMBODIMENTS

Figure 1:
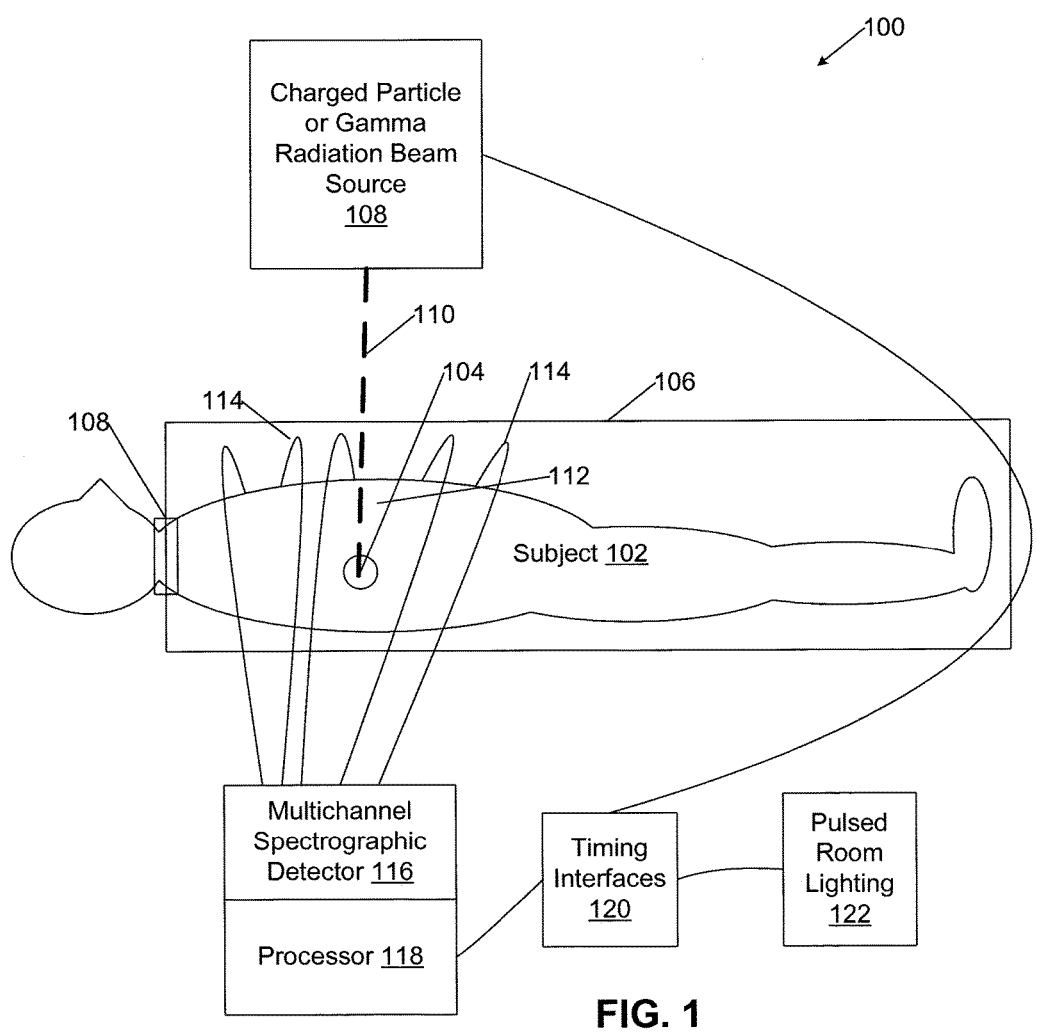
FIG. 1 is an illustration of a system for performing monitored radiotherapy.

A system 100 for providing radiotherapy and monitoring factors known to affect the effectiveness of radiotherapy, and monitoring effects of radiotherapy on tissue, is illustrated in FIG. 1.

Portions of a subject 102 containing a tumor 104 requiring radiotherapy are placed within an enclosure 106 for excluding light. The enclosure 106 may be made of black plastic or cloth, and has a sealing portion 108 drawn tight by an elastomeric band such that a subject's eyes may be permitted access to ambient light and thereby prevent claustrophobia while still excluding room light from optical fibers 114. It is anticipated that a variety of enclosures 106 may be provided to exclude light from various portions of a subject in various embodiments, in some embodiments light may be excluded from a subject's cranium, in others from a subject's chest or abdomen, according to location of tumor 104 within subject 102 and desired beam angles.

An accelerator 108, or other device for providing high energy radiation, is aimed to provide a beam 110 of radiation through normal tissue 112 to tumor 104. In an embodiment, the accelerator 108 provides a beam of electrons having energy of 6 million electron volts (6 MeV) or greater, in a particular embodiment the beam energy lies between 6 and 24 MeV. In an alternative embodiment, the device for providing high energy radiation provides photons having sufficiently high energy (6 MV to 18 MV) that Compton scatter electrons are energetic enough to emit Cherenkov radiation. In yet another alternative embodiment, the accelerator 108 provides a proton beam. In an alternative embodiment, the radiation source is implanted in the body, inducing Cherenkov emission light as charged particles are emitted during radiation decay. The subject 102 and enclosure 106 is positioned within a room having subdued lighting.

Since high radiation doses are desired in tumors, while high doses are not desired in surrounding normal tissue or on skin because those tissues can be damaged by radiation, provisions are typically made for varying arriving beam angles by, for example, rotating the subject and enclosure in the beam, rotating the radiation source about the subject and enclosure, or periodically interrupting treatment to reposition the subject and enclosure.

At least one, and in an embodiment an array of many, optical fibers 114 are provided and positioned, such as in contact with or close to, subject 102 in enclosure 106, for collecting any light that may be emitted from subject 102. In an alternative embodiment, a camera system, having a lens system adapted to collecting light from the subject and an array photosensor for detecting the collected light, positioned some distance from the subject is used to image light emitted from the tissue.

Optical fibers 114 provide light to multichannel spectrographic detector 116. For each channel of the multichannel spectrographic detector 116 there is a wavelength-dependent dispersive device such as a prism or diffraction grating for separating light according to wavelength, and an array of photosensors such as a CCD sensor, an array of PIN diodes, or an array of photomultiplier tubes. In particular embodiments, optical filters are inserted in the detection channel before the spectrograph to reduce ambient light and Cherenkov emission above or below a specified wavelength range, thus reducing the required dynamic range of the detector.

Detector 116 provides information indicative of received light amplitude at each of many wavelengths to processor 118. Processor 118 analyzes this information to provide indications of heme concentration in tumor, oxygen concentration in tumor, and other parameters (such as metabolic activity and oxygenation) provided by photo-luminescent emission.

In an alternative embodiment, detector 116 is a spectrally sensitive detector constructed of a filter wheel and photodetector, providing spectral information on captured light from fiber 114 by alternately interposing an assortment of filters each having a passband at a wavelength of interest. In an alternative embodiment, a tunable filter is used in place of a filter wheel. In another alternative embodiment, a filter wheel or tunable filter is placed in front of a camera positioned some distance from the subject. This embodiment allows collection of a series of images, each image of the series imaging light from the subject at a different wavelength band, to allow spectral analysis on the series of images.

Figure 2:
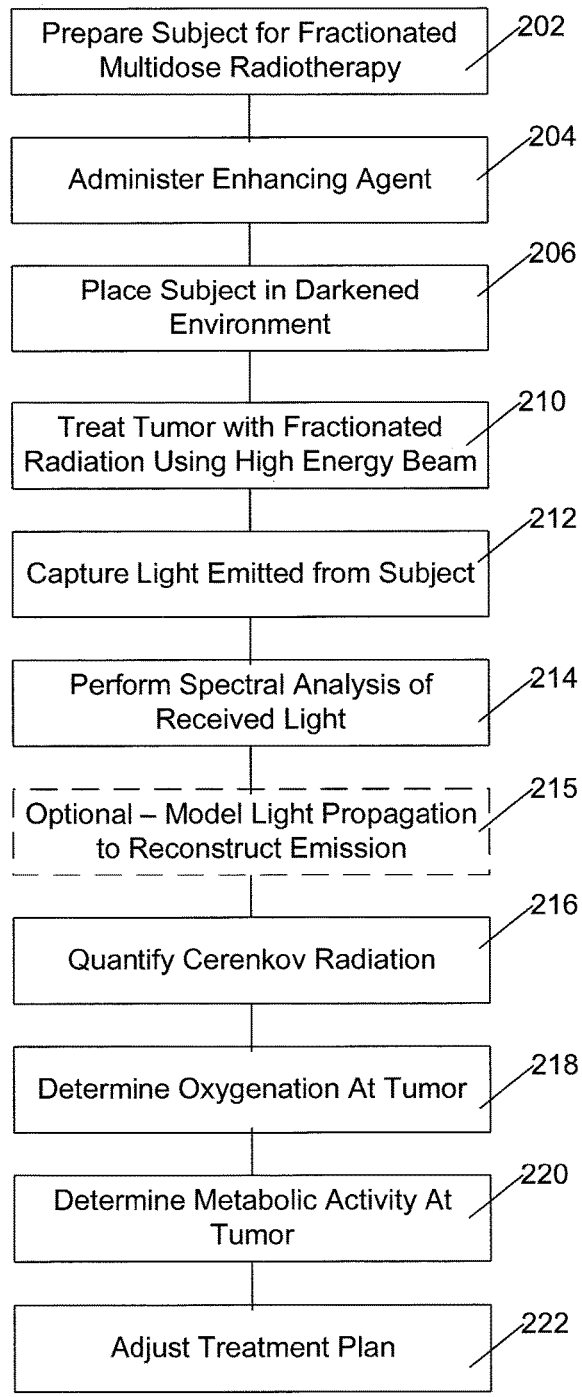
FIG. 2 is an approximate flowchart of a method of monitoring radiotherapy.

The system 100 is operated according to a method illustrated in FIG. 2. The subject is prepared 202 for multidose radiotherapy as known in the art of radiotherapy; tumor 104 is localized and imaged, alignment marks may be applied by tattoo or in other ways, and aiming and positioning masks or frames may be made. A desired dose of radiation for each session is prescribed.

Some naturally occurring fluorescent or phosphorescent substances, including protoporphyrin IX (PpIX), and cytochrome-C are present normally in tissues. DNA is also weakly fluorescent. These substances may be excited by, and thus give a characteristic glow, by absorption of Cherenkov radiation.

In an embodiment, prior to each session for which monitoring is desired, a fluorescence-enhancing and indicating agent is administered 204. In an embodiment, the enhancing and indicating agent is a dose of 20 milligrams per kilogram body weight of 5-delta-aminolevulinic acid (5-ALA), the dose being administered an incubation time of approximately four hours before each divided radiotherapy session begins.

In metabolically active tumor 104, some of the 5-ALA is metabolized to Protoporphyrin IX (PpIX). In alternative embodiments, it is expected that other enhancing agents may be developed or utilized. PpIX production in normal tissue 112 and tumor 104 is due to metabolic processes in those tissues and a quantity of PpIX produced in those tissues is dependent on an amount of metabolic activity in those tissues.

In alternative embodiments, other enhancing and indicating agents are used as enhancing and indicating agents. In a particular embodiment an antibody specific to the tumor is tagged with a fluorophore and administered as a fluorescence-enhancing and indicating agent.

The subject 102 is then placed 206 in a darkened environment, which in an embodiment includes placing those parts of the subject to be subjected to radiotherapy within enclosure 106, and positioning light collecting fibers 114 to collect light from the subject 102, as heretofore described with reference to the enclosure.

The tumor is then treated 210 by having accelerator 108 then provide a beam of high energy radiation aimed along a beam path at tumor 104 to perform radiotherapy of the tumor. In an embodiment, the subject 102 may be rotated during the session to distribute radiation absorbed by normal tissues 112 while maintaining beam targeting at tumor 104.

As charged particles of, or induced by, beam 110 decelerate in both normal tissue 112 and tumor 104, these particles generate light by Cherenkov radiation, with broadband spectral constituents decreasing with wavelength to the inverse square power.

Some of the light generated by Cherenkov radiation propagates to light collecting fibers 114, and some may be absorbed by fluorophores (or phosphors) within subject 102, including fluorophores (or phosphors) within normal tissue 112 and tumor 104. Among fluorophores within subject 102 are any PpIX produced from metabolic activity in tissue 112 and tumor 104. Light from Cherenkov radiation that is absorbed by fluorophores (or phosphors) in tissue and tumor may stimulate photo-luminescent emission by those tissues and tumor.

Light from both Cherenkov radiation and photo-luminescent emission propagates from the beam path to a surface of the subject 102, intersecting any tissue between the tumor and the surface, and being attenuated by absorption from molecular absorbers such as deoxyhemoglobin, oxyhemoglobin, proteins, lipids and water before being emitted from the subject.

The dominant absorption is from deoxyhemoglobin and oxyhemoglobin, which differ in their spectral absorption, and so changes in spectral characteristics of the attenuated light emitted from the subject are a reasonable measure of oxygen saturation of the blood in the region.

Protoporphyrn IX (PpIX), formed in tissue from 5-ALA as part of the heme synthesis pathway that is often upregulated in many tumors, absorbs across the visible spectrum, with a large absorption in the blue Soret band. This absorption leads to fluorescence emission from PpIX in the 640-720 nm wavelength range.

Light emitted from the subject 102, both of Cherenkov origin as modulated by absorption in tissue and tumor, and of fluorescent (or phosphorescent) origin, and attenuated by molecular absorbers in the subject, is captured 212 by fibers 114. This light is directed to multichannel spectrographic detector 116, which performs a spectral analysis of received light. Electronic spectrographic signals indicative of light amplitude at each of several wavelengths of interest are provided from spectrographic detector 116 to processor 118 for processing.

In an embodiment, processor 118 utilizes a model of light propagation from the beam path through a model of subject 102 to determine a spatial model of light emitted within, and light attenuation within, subject 102 and tumor 104. It is expected that such an embodiment could offer enhanced accuracy over an uncorrected system. In an embodiment, a Monte-Carlo or diffuse photon propagation model is used.

In an alternative embodiment, beam 110 is directed at tumor 104 from multiple angles through tissue 112 within each treatment session. In such an embodiment, processor 118 uses information regarding beam angle to correlate measurements such that tumor oxygenation and tumor metabolic activity determined during one session is compared with tumor oxygenation and metabolic activity determined along a similar beam angle in other sessions.

Processor 118 quantifies Cherenkov emission 216 in tumor and total hemoglobin from an amount of light measured at one or more wavelengths to which oxyhemoglobin and deoxyhemoglobin are isosbestic.

Processor 118 quantifies percent oxygenation 218 of hemoglobin in tumor from light quantity received at 2 specific wavelength bands such as bands centered at 750 nm and 580 nm wavelengths. Alternatively the measured spectral characteristics of light captured by fibers 114 are curve-fit to pre-measured Cherenkov emissions spectra and transmission attenuation data obtained from samples of liquid with blood and water that have been oxygenated and deoxygenated.

Processor 118 quantifies metabolic activity 220 of tumor 104 by quantifying fluorescent emission from PpIX by quantifying received light from fibers 114 in the 640-720 nanometer wavelength band, and applying any corrections provided in the embodiment. In alternative embodiments, these corrections may include corrections from a Monte-Carlo or diffusing photon propagation model of the tissue.

The stimulation of fluorescence emission by protoporphyrin IX can be taken as a signal which is proportional to the amount of PpIX produced, and this is indicative of metabolic activity in the tumor. Destruction of cellular mitochondrial function through radiation damage due to the applied radiotherapy would appear in some embodiments as a reduction of PpIX production, and hence a decrease in light emitted at PpIX fluorescent wavelengths versus light emitted at Cherenkov wavelengths in the detected spectrographic signals.

In an alternative embodiment, fluorescent emissions from another metabolite are used as a fluorophore for tracking metabolic activity of tumor 104, the fluorophore being excited by the Cherenkov radiation. In alternative embodiments, the fluorescent emission could be used to track the activity of an alternative enhancement agent, such as antibodies or antibody fragments to cell surface receptors tagged with a fluorescent (or phosphorescent) dye. In yet other alternative embodiments, fluorescent emissions from NADH or NAD excited by the Cherenkov radiation are used as indicators of metabolic activity within tumor 104.

Since radiation damage to tumor cells during radiotherapy involves free radical reactions, it is expected that treatment effectiveness will depend somewhat on the relative oxygenation of heme at the tumor 104 as monitored by processor 118. Further, changes in metabolic activity in tumor 104 from a first treatment session to a later second treatment session as measured by PpIX or other fluorescent emissions measured by processor 118 are also expected to be indicative of treatment effectiveness. In fractionated radiotherapy subjects may receive as many as 30 to 40 fractions of a total radiation dose, each fraction being administered on a separate day as part of a total treatment series. During the treatment series, changes in tumor metabolic activity are expected if the tumor is responsive to therapy. It is expected that metabolic signal changes would occur as a decrease in the fluorescent signal over time if the patient is responding to therapy.

These measures of treatment effectiveness are presented to a physician and used to adjust 222 the treatment plan, both of the radiotherapy and following adjunct therapies such as chemotherapy.

In an embodiment, multiple spectrographic analyzers are provided, each coupled to receive Cherenkov and fluorescent emissions from a different point on the subject through separate pickup fibers. In this embodiment, diffuse optical modeling or Monte Carlo modeling software executing on processor 118 allowing reconstruction of a shape and spectral characteristics of an emissions zone within the subject, and for determining spectral characteristics of light emitted within the tumor as opposed to light emitted elsewhere (such as in normal tissues) in the subject by compensating for changes due to light transport in surrounding tissues. The diffuse optical modeling software provides for more accurate estimation of the fluorescent emissions thereby refining the measurements to more directly inform about pertinent areas of tissue.

In an alternative embodiment, light emissions from the subject are sampled only from certain predetermined beam locations or from certain predetermined locations within the subject, with the goal of maximizing information from non-tumor tissues. Also, in an alternative embodiment, comparison of measurements of emitted light spectra from tumor and non-tumor regions is performed to accurately calibrate data to the individual subject, making interpretation of changes over different days more reliable.

In an alternative embodiment, in addition to collecting fibers 114 placed at a surface of subject 102, there are additional optical collecting fibers (not shown) placed within body cavities or, in some alternative embodiments, even directly implanted in tumor 104. Light from such fibers is processed by spectrographic detector 116 and processor 118 in a manner similar to that stated herein for light from fibers 114. Such additional collecting fibers may permit improved accuracy by enabling the system to track light signals which do not propagate well in tissue, or minimizing the spectral distortion of light passing through tissue to the detector. In an alternative embodiment, implantation of fibers onto surfaces or in cavities is incorporated as part of radiation therapy preparation.

Measurement of emission stimulated by radiation emitted from implanted radio-isotope sources, such as brachytherapy seeds is feasible, and can allow direct measurement at the tissue site where the radiation is imparting maximal energy. Implanting fiber optic measurements at these sites is feasible via fiber optics or small photodiode arrays. Following the same procedures as above, the tissue function or blood oxygen saturation could be probed during the prolonged delivery of radiation during brachytherapy radiation delivery.

Many sources of high energy charged-particle beams, including cyclotrons and some other particle accelerators, provide pulsed beams. Further, the human visual system is known to integrate received light, so that black intervals that are short enough, and repeated rapidly enough, may not be noticed by a human subject. In an alternative embodiment, therefore, the enclosure 106 is omitted. The treatment room is sealed to exclude all natural and uncontrolled artificial light. Timing interfaces 120 are provided for determining intervals of beam transmission, and for controlling pulsed room lighting 122.

In operation, the timing interfaces 120 controls an effective shutter (FIG. 5) interval 200 of the spectrographic detector 116 to effectively consider only light received by the cameras in an interval 202 during and/or surrounding pulses of, and including a fluorescent or phosphorescent decay interval 204 after, pulses 206 of the beam. Timing interfaces 120 also controls and pulses room lighting such that the shutter interval does not overlap pulses 208 of the room lighting. Light received at the spectrographic detector 116 during multiple shutter intervals is totalized, in an embodiment at the camera, and in an alternative embodiment multiple images are captured and per-channel spectrographic light totals are totalized by processor 118.

Figure 3:
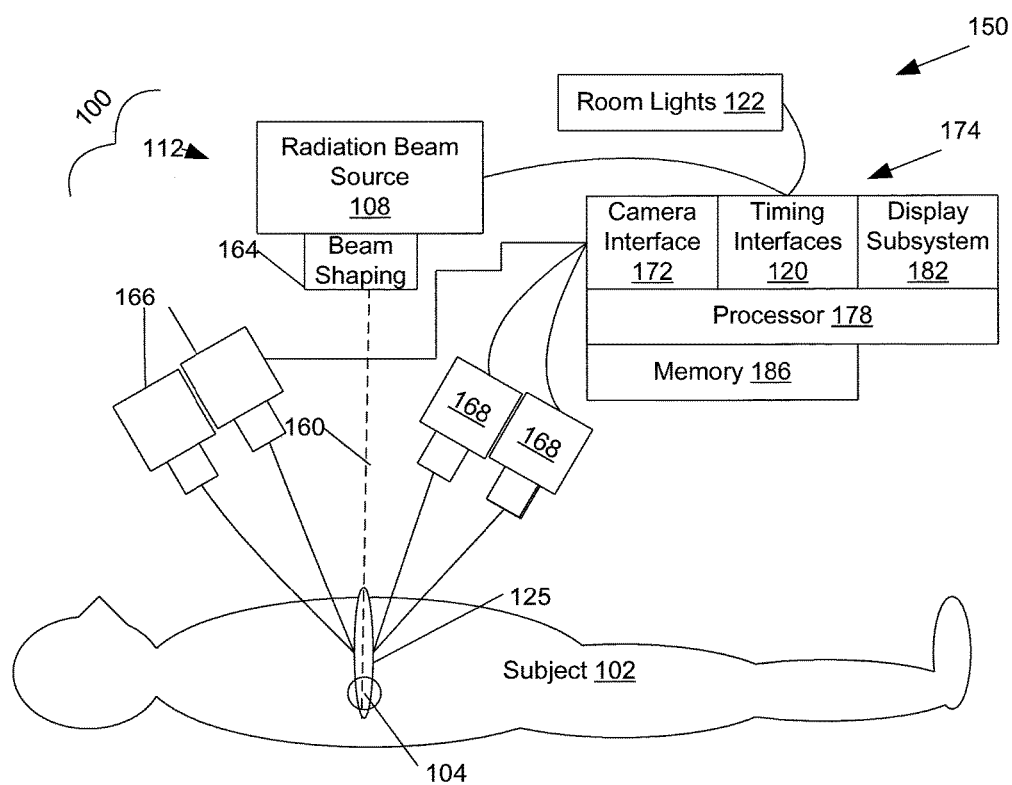
FIG. 3 is an illustration of an alternative embodiment of a system for performing monitored radiotherapy with time-controlled room lighting and camera sensing of light emissions from a subject.

In an alternative embodiment 150 (FIG. 3), as an alternative to optical fibers 114 and multichannel spectrographic detector 116, high-sensitivity electronic cameras 166, 168, are used to image Cherenkov light and localize locations on the subject where this light is emitted. In another alternative embodiment, some optical fibers 114 and multichannel spectrographic detectors 116 are provided, with the fibers placed in particular tumor locations, and electronic cameras 166 are provided for imaging light escaping from the subject. In a particular embodiment for imaging and discriminating between both Cherenkov and fluorescent emissions from short-persistence, naturally-occurring, or metabolically-induced fluorophores including PpIX, the cameras are ICCD cameras capable of nanosecond-range shutter intervals.

A subject 102 is positioned in the path of a radiation beam 160 such that the beam intersects tumor 104. Beam 160 is provided by an accelerator 108, or other device for providing high energy radiation, and is typically shaped by beam-shaping apparatus 164.

The subject 102 is located within an environment that excludes daylight, and light from uncontrolled sources, such as fluorescent lamps, is also excluded.

In an embodiment, a drape or paint of a light-absorbing material is provided so that stray light emitted from the subject 102 and not absorbed by a camera 166, 168 is absorbed.

In an embodiment, the accelerator 108 provides a beam of electrons having energy of 6 million electron volts (6 MeV) or greater, as used to provide treatment energy to deep tumors as opposed to treatment of surface skin. In a particular embodiment the beam energy lies between 6 and 24 MeV. In an alternative embodiment, the accelerator 108 produces a photon beam of 6 MV or greater capable of inducing energetic photons by Compton scatter. In another alternative embodiment, the accelerator 108 provides a high-energy proton beam.

At least one camera 166 is used to capture the images, and in an embodiment a second or more cameras 168, are positioned to provide multiple images of Cherenkov and fluorescent radiation emission from subject 102. In an embodiment, multiple cameras with a defined spacing between them at each camera location may be provided.

The cameras 166, 168 are coupled to camera interface 172 of image processing system 174; camera interface 172 captures and stores digital images from the cameras 166, 168, in memory 186 for processing by at least one processor 178 of the image processing system 174. In addition to interfaces to the camera interface 172 and memory 186, processor 178 interfaces with a timing interface 120 and a display subsystem 182. Timing interface 120 is adapted to determine timing of pulses of radiation from the radiation beam source 108, to control pulsed room lighting 122 to avoid interference from room lighting in the way discussed with reference to FIG. 5, and to synchronize light or image capture by spectrographic detector 116 or cameras 166, 168 at shutter intervals discussed with reference to FIG. 5.

As the beam penetrates subject 102, Cherenkov light is emitted within an emissions zone 125, including the tumor 104.

In an embodiment, the cameras 166, 168 are spectrally-sensitive cameras capable of providing spectral data permitting distinction between Cherenkov and fluorescent light, and in a particular embodiment permitting distinction between oxyhemoglobin and deoxyhemoglobin. Spectrally-sensitive cameras suitable for this application may be implemented as black and white cameras equipped with apparatus for positioning filters in front of each camera, such as rotatable multiple-filter disks; by deposition of custom filter elements in a pattern on pixel sensors of a photosensor array as is common for color cameras; or in other ways.

While Cherenkov radiation is emitted during beam pulses 206 (FIG. 5), light emitted 209 from naturally occurring, artificially administered, and drug metabolite fluorescent materials within a subject, including PpIX, lags the beam and decays exponentially after each pulse of the beam turns off as illustrated. In an embodiment therefore, an effective shutter interval during beam pulse 206 is used to image light primarily emitted by Cherenkov mechanisms, and an effective fluorescent shutter interval 211 is used to capture light emitted from the subject or phantom by fluorescent and phosphorescent mechanisms. In a particular embodiment, the beam pulses 206 are of duration 5 microseconds. In this embodiment, light arriving in fibers 114 or light imaged by cameras 166, 168, is recorded as image pairs, with a first image of each pair indicative of light emitted during beam pulse 206 and a second image of each pair indicative of light emitted during the fluorescent shutter interval 211. Processor 118 or 178 executes machine-readable instructions in associated memory, such as memory 186 to reconstruct first tomographic image sets of the subject from the first images of all image pairs captured, to reconstruct second tomographic image sets of the subject from the second images of all image pairs captured, and the ratios or otherwise processes the first and second tomographic image sets to determine a tomographic image set of fluorophore distribution in the subject.

In embodiments, such as those where 5-ALA is administered, where the fluorophore distribution is related to metabolic activity in the subject, the tomographic image set of fluorophore distribution in the subject is then indicative of metabolic activity in the subject. The processor 118 or 178 further executes machine readable instructions in memory to compare the tomographic image set of fluorophore distribution in the subject against a tomographic image set of fluorophore distribution obtained during a prior radiation treatment session to produce a tomographic image set indicative of treatment effectiveness.

Figure 5:
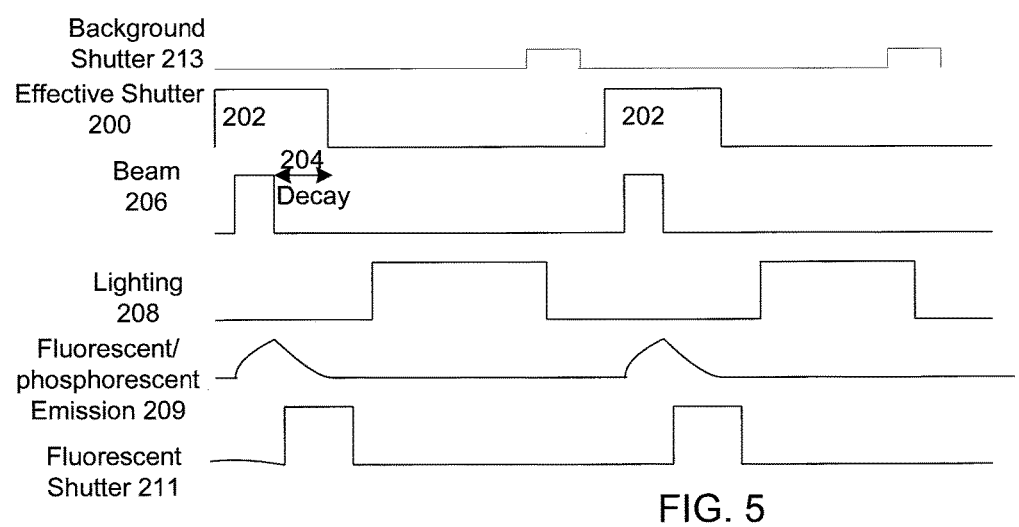
FIG. 5 is an approximate timing diagram of time windows showing relationships of room lighting, beam pulses, and camera shutter windows.

In yet another alternative embodiment, low, but steady or "DC", ambient light is permitted in a treatment room; timed room lighting 208 is not used. The beam is pulsed 206, in a particular embodiment with approximately 5 microsecond pulses repeating at an approximately 150 hertz rate. Cherenkov radiation is emitted during beam pulses 206 (FIG. 5). An effective shutter interval coincident with beam pulse 206 is used to make a first image of light primarily emitted by Cherenkov mechanisms; this light is contaminated with the ambient light. A second or background effective shutter interval 213 is used to make a second or background image of light resulting from the steady ambient light. In this embodiment, the second image is subtracted from the first image to produce each image of Cherenkov light. In essence, light arriving in fibers 114 or light imaged by cameras 166, 168, is recorded as image pairs, with a first image of each pair indicative of light emitted during beam pulse 206 and a second image of each pair indicative of light during the background shutter interval 213. Processor 118 or 178 executes machine-readable instructions in associated memory, such as memory 186 to subtract the second image of each pair from the first image to produce each image of Cherenkov light.

Since all three embodiments: an enclosure 106 surrounding and excluding ambient light from the subject; the combination of timing interfaces 120 configured to capture a first image when beam is on and a second image when beam is off and fluorescent emissions decayed, with machine readable instructions to determine Cherenkov light by subtracting the second image from the first image; and the combination of timing interfaces 120 and pulsed room lighting 122 all serve to prevent interference of room lighting from interfering with measurement of Cherenkov radiation and fluorescent radiation emitted from an emissions zone in the subject, the term "apparatus for preventing interference by room lighting" as used herein shall mean one or more of an enclosure 106 surrounding and excluding ambient light from the subject, the combination of timing interfaces 120 and pulsed room lighting 122, and the combination of timing interfaces configured to capture first and second images and determine a Cherenkov or a fluorescent image by subtraction.

Since Cherenkov light is not intense, in embodiments light received by the detectors, including cameras 166, 168 or spectrographic detector 116, is summed during, or averaged over, multiple shutter intervals.

It is occasionally desirable to image, or measure an approximate dose of, a radiation beam as it impacts a subject's skin. Where it is desirable to measure dose at skin surface to verify proper operation of accelerator 108, an optical fiber 114 is placed to collect light from an expected entry point of the beam into the skin; or spectrally-sensitive cameras 166, 168 are aimed to collect light from the expected entry point of the beam into the skin. Light captured by fiber 114 or camera 166, 168 will then be a combination of Cherenkov light emitted in the skin at the point of beam entry, and Cherenkov light emitted from deeper levels in the subject. Since Cherenkov light emitted from deeper levels in the subject is attenuated by chromophores, such as hemoglobin, in the subject, contributions to light as captured by fiber 114 or camera 166 from these deeper levels has different spectral characteristics than the light emitted directly from the skin; processor 118, 178 therefore processes the captured images to partially remove contributions from Cherenkov light emitted at deeper levels. The resulting image is provided to system operators so that they may verify correct aiming of the beam, and correct settings of beam shape and intensity.

Cherenkov radiation and associated fluorescent and/or phosphorescent emissions are useful for beam profiling and calibration as well as for monitoring treatment.

Figure 4:
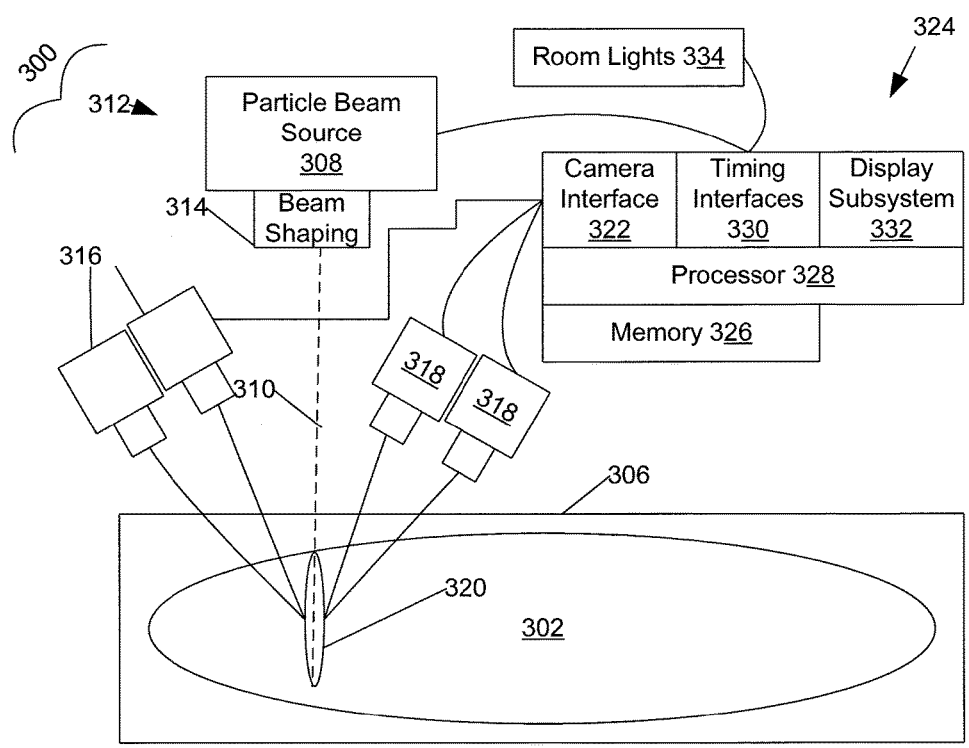
FIG. 4 is a block diagram of apparatus for determining beam profiles of high energy radiation for use in radiotherapy.

A system 300 for providing radiotherapy equipped with a subsystem for determining beam profiles is illustrated in FIG. 4.

A beam-calibration phantom 302 is placed in a zone where it is desired to measure a profile of a radiation beam 310 provided by a radiation treatment machine 312. The zone may be a volume above or beside a treatment table 306. In many embodiments, the phantom is a fluid-filled tank, the fluid in the tank being a transparent fluid having an index of refraction greater than that of air and a tissue equivalent density and or chemical composition; in a particular embodiment the transparent fluid is water. In an embodiment, the tank has no top, or a transparent top, and transparent sides such as glass or transparent plastic. In a particular embodiment the tank has sides constructed of acrylic sheets; another particular embodiment has sides constructed of polycarbonate panels. In an embodiment, a small amount of scattering agent is added to the liquid in the tank to enhance scatter of Cherenkov light but not affect propagation of the radiation beam, thereby overcoming directionality of Cherenkov light and allowing more light to be detected laterally around the tank. The treatment room may be blacked out to prevent interference of ambient light with measurements of the Cherenkov radiation because a phantom is not subject to claustrophobia like live subjects.

In an alternative embodiment, the tank is filled with a transparent fluid having an index of refraction greater than that of water, such as silicone oil. In yet another embodiment, the phantom is formed from a high-index, transparent, material, such as a cast high-index plastic, and may have one or more of fluorophores, phosphors, and light-scattering additives embedded within it. In yet another embodiment, the phantom is formed from a transparent scintillating material; in a particular embodiment the transparent scintillating material is a long-persistence material having a decay time of about 400 nanoseconds or longer, and tissue-equivalent radiation absorption. Long-persistence fluorophores and scintillating materials may permit operation with less expensive cameras having coarser shutter timing and/or longer shutter intervals than the nanosecond-range-capable ICCD camera used in another particular embodiment with short persistence or naturally-occurring fluorophores like PpIX.

The treatment table 306 and phantom 302 are located within an environment that excludes daylight, and light from uncontrolled sources, such as incandescent and fluorescent lamps, and LED indicator lights, is also excluded. In another embodiment, the phantom walls are coated on their interior surface with a light-absorbing coating except for camera viewing windows positioned in front of each camera, the coating is provided to absorb both stray light originating from outside the phantom and to prevent Cherenkov light from being reflected from the phantom wall into a camera to give a false indication of beam profile.

In an embodiment, a drape of a light-absorbing material is provided so that stray light emitted from Cherenkov radiation zone 320 and not absorbed by a camera is absorbed.

An accelerator 308, or other device for providing high energy radiation, is aimed to provide a beam 310 of radiation through beam-shaping apparatus 314 to phantom 302. In an embodiment, the accelerator 308 provides a beam of electrons having energy of 6 million electron volts (6 MeV) or greater, in a particular embodiment the beam energy lies between 6 and 24 MeV. In an alternatively embodiment, the accelerator 308 produces a photon beam of 6 MeV or greater. In an alternative embodiment, the accelerator 308 provides a proton beam.

Figure 6:
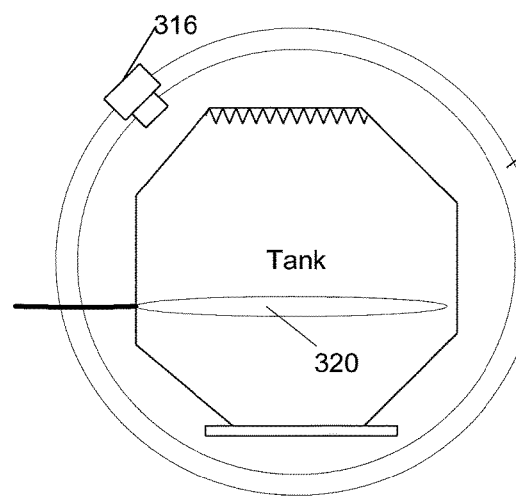
FIG. 6 illustrates a system utilizing a single camera, or camera pair, on a rotating mount for determining profiles of high energy radiation for use in radiotherapy.
Figure 7:
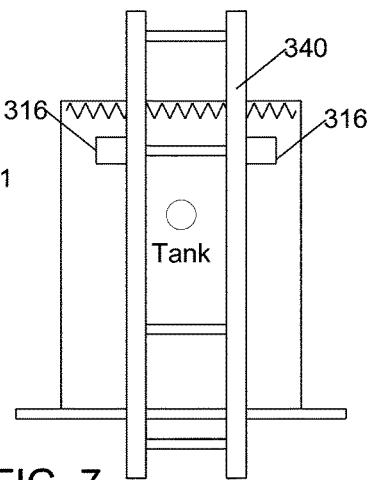
FIG. 7 illustrates the system of FIG. 3 from a different angle.

At least one camera 316 is used to capture the images, and in an embodiment a second or more cameras 318, are positioned to provide multiple images of the Cherenkov radiation emission zone 320 where beam 310 intersects the transparent fluid of phantom 302. In an embodiment, as illustrated in FIG. 4, a pair of cameras is used by providing two cameras 316 with a defined spacing between them at each camera location, allowing imaging of the beam with or without tomographic recovery. In an alternative embodiment as illustrated in FIG. 6, a single camera 316; or in a variation as illustrated in FIG. 7, a single camera pair 316 is provided; the embodiments of FIGS. 6 and 7 mount the camera or camera pair on a rotary, movable, mount 340 such that single images, or stereo pairs of images, can be made of the Cherenkov emissions zone from several camera positions, In the interest of simplicity, structure and bearings for supporting the rotary mount 340 and motor 341 has not been shown. The embodiment of FIG. 7 illustrates the beam entering the tank from out of the page.

Figure 8:
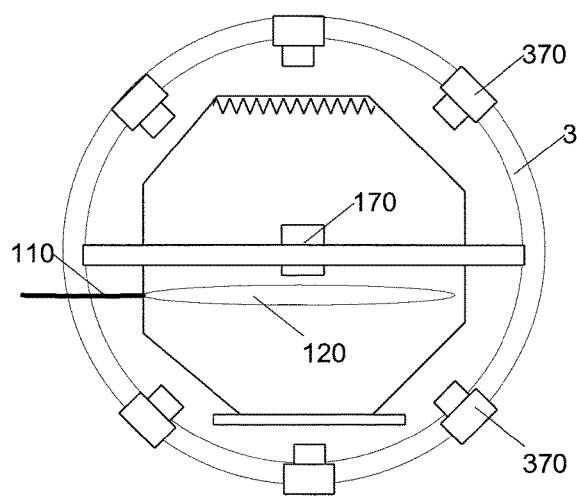
FIG. 8 illustrates a system having multiple cameras on a fixed mount outside the tank
Figure 9:
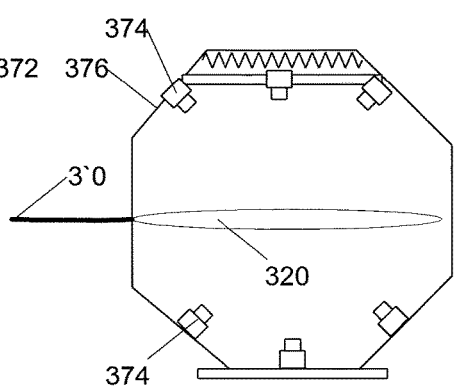
FIG. 9 illustrates a system having multiple cameras mounted inside the tank.
Figure 10:
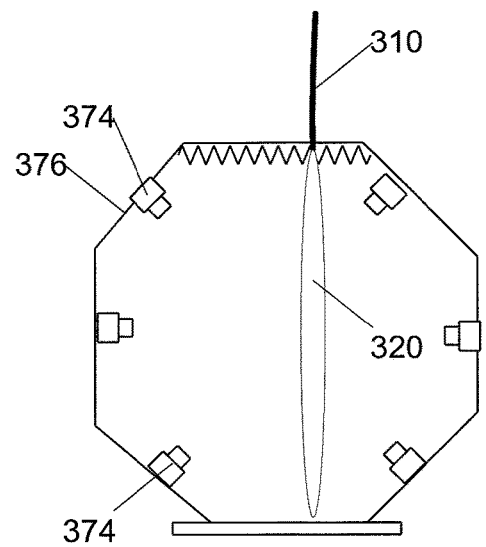
FIG. 10 illustrates a system having the beam enter the tank from above the tank.
Figure 12:
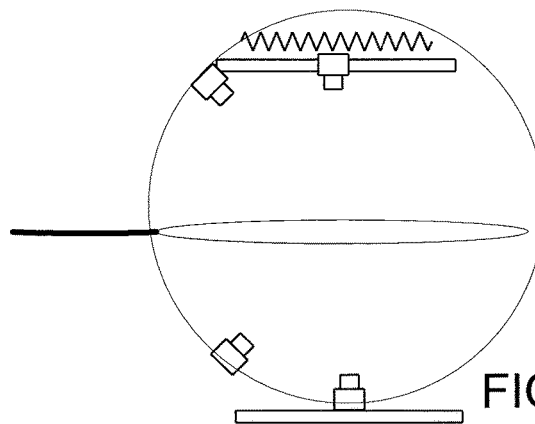
FIG. 12 is an illustration having a spherical or cylindrical tank with internal cameras, with the tank mounted on a rotary mount.
Figure 11:
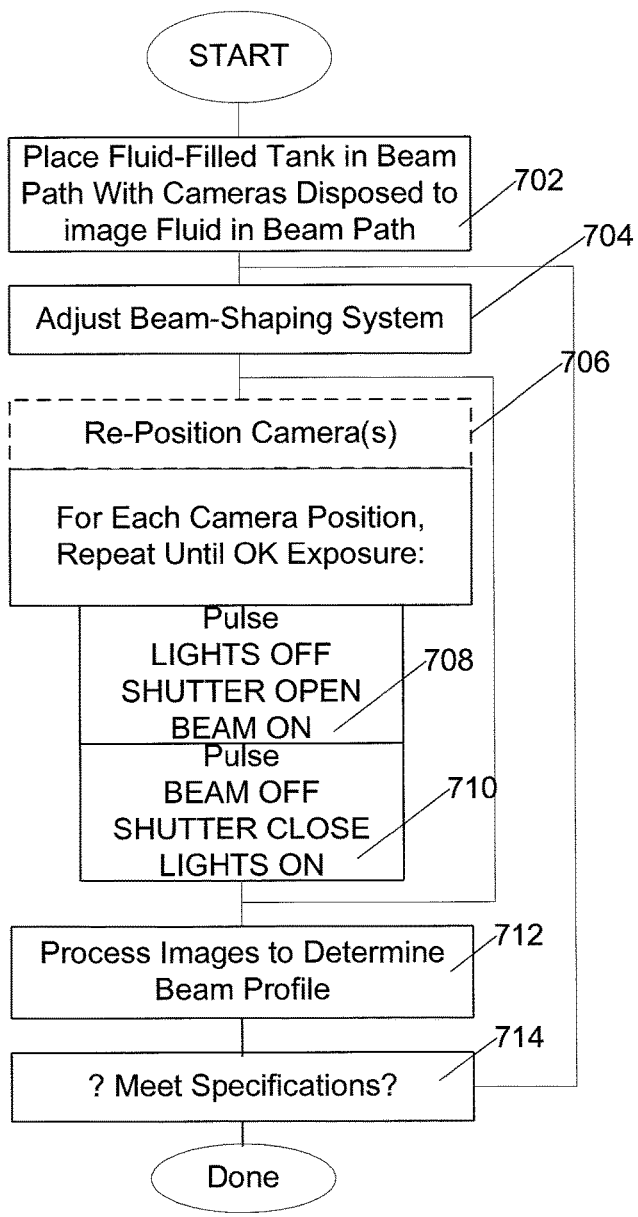
FIG. 11 is a flowchart of a method of determining beam profiles of high energy radiation for use in radiotherapy.

While the embodiments of FIGS. 6, 7, 8, and 9 illustrate the beam entering the tank from a side of the tank, the method is applicable to beams entering the tank from any angle, including by way of example a beam as illustrated in FIG. 10. where the beam comes from above the tank.

The cameras 316, 318 are coupled to camera interface 322 of image processing system 324; camera interface 322 captures and stores digital images from the cameras 316, 318, in memory 326 for processing by at least one processor 328 of the image processing system 324. In addition to interfaces to the camera interface 322 and memory 326, processor 328 interfaces with a timing interfaces 330 and a display subsystem 332.

In an alternative embodiment, as illustrated in FIG. 8, a plurality of cameras 370 are disposed on a fixed frame 372 outside the volume of the phantom but configured to provide images of the emissions zone 320 from several angles.

In an alternative embodiment, as illustrated in FIG. 9, a plurality of submersible cameras 374 are disposed within the volume of the phantom and configured to provide images of the emissions zone 320 from several angles. In a particular embodiment, submersible cameras 374 are cemented to a wall of phantom 376.

In a particular embodiment, a camera is disposed to image the emissions zone from approximately every 60 degrees in the horizontal plane, into which the radiation beam is being sent. The camera field of view is designed to capture the relevant depth of the beam into the tank from above, and the depth of focus of the cameras is designed to capture light from the entire cross section of the beam. The angular arrangement is chosen to allow capture of the beam profile data in a time which matches with the temporal requirements of characterizing the beam. For example, fast beam profile changes or complex beam cross section shapes require more cameras and less mobile cameras, for fast profile imaging.

Camera numbers and viewing angles may in some embodiments be determined according to the expected beam profile; for example standard square beam cross sections may only require one or two cameras to characterize the beam, and may not even require tomographic recovery to characterize the beam. Where imaging time is unconstrained, beams may be imaged with a rotation stage or rotating frame for sequential imaging of the beam from multiple angles. A standard square beam may be adequately profiled by only two camera positions at 90 degrees from each other, whereas a non-square or non-circular beam would require more camera positions for tomographic recovery of the profile. If adaptive delivery of radiation such as arc therapy or intensity modulated radiation therapy are imaged, then multiple parallel cameras would be desirable to allow imaging of the complex beam cross sections in reasonable or in real time during delivery to the tank. The time constraints and complexity of the beam therefore determine the exact number of cameras and degree of sequential or parallel acquisition required.

In each embodiment, the phantom 302 is positioned 702 in the beam, and beam adjustment devices, if any, are adjusted 704 to provide a particular beam profile. The cameras 316, 318, 370, 374 in all embodiments are disposed to provide images of the Cherenkov radiation emissions zone 320, where beam 310 intersects fluid of phantom 302, and may be repositioned 706 if movable camera mounts are used. It should be noted that, because cameras are likely to be damaged if the beam directly impinges on the camera, movable mount 340 is configured, and the cameras are located, to avoid direct impingement of the beam on any camera.

In each embodiment, image and/or stereo pairs of images each are taken by sequentially 708 turning OFF room lighting, opening effective or physical camera shutters, pulsing the beam, then sequentially 710 turning off the beam, closing shutters, and turning ON room lighting. This process results in multiple images taken from multiple angles of Cherenkov radiation zone 320 by cameras 316, 318, 370, 374. Once sufficient images are captured, they are processed 712 by processor 328 to reconstruct a fully three dimensional, tomographic, image of the Cherenkov emission, which is a surrogate of the beam profile.

Prior to reconstruction of the beam profile from the images, the images obtained by any cameras located outside the phantom volume (such as those of FIGS. 4, 6, and 8) are corrected for distortions caused by refraction as light passes from the emissions zone 320 through known surfaces of the phantom.

A combination of rotation angles both vertical and lateral around the beam may be used.

The multiple camera image formation by tomography would use a filtered backprojection computational algorithm for recovery of the emissions zone 320.

It is known that Cherenkov emissions from beams of intensities used during radiotherapy are somewhat dim, hence sensitive cameras with multiple, brief, summed exposures or long, integrated, exposures may be required, and it is also advisable to avoid interference from extraneous lighting sources.

Timing interfaces 330 are arranged to sense a timing of beam pulses provided by particle beam source 308 and to control room lighting 334 such that room lighting is pulsed and does not overlap pulses of beam 310. Similarly, timing interface 330 is arranged to control capture of images at camera interface 322 from stereo camera pairs 316, 318 to capture images of light emitted at emission zone 320 during pulses of beam 310, and to ignore light received by camera pairs 316, 318, during pulses of room lighting. It is anticipated that room lighting 334 may be provided by fast-responding light emitting diode arrays.

In operation, the timing interfaces 330 controls an effective shutter (FIG. 5) interval of the cameras or stereo camera pairs 316, 318, 370, 374 to effectively consider only light received by the cameras in an interval 202 surrounding pulses of the beam. The timing interfaces 330 also controls and pulses room lighting such that the shutter interval does not overlap pulses of the room lighting. Light received at the cameras 316, 318, 370, 374 during multiple camera intervals is totalized, in an embodiment at the camera, and in an alternative embodiment multiple images are captured and pixel light totals are totalized by processor 328.

Once sufficient light is received at cameras 316, 318, 370, 374 during the shutter intervals and totalized images prepared in or read through camera interface 322 into memory 326, the beam is shut off. Then at least one processor 328 processes the images in memory 326, to construct a three-dimensional model of light emissions in the emission zone 320. Since the light emissions in the emissions zone are from Cherenkov radiation emitted as charged particles directly of or secondarily produced by beam 310 decelerate in the fluid of the phantom, with broadband spectral constituents decreasing with wavelength to the inverse square power, these light emissions relate directly to radiation dose from beam 310 passing into and absorbed in the emissions zone 320. Further, since Cherenkov radiation is emitted from where the beam intersects fluid of the phantom in emissions zone 320, and not from surrounding un-irradiated fluid, the reconstructed three dimensional model of light emissions in emissions zone 320 provides an indication of beam shape.

The processor 328 then uses calibration tables of emissions to dose in its memory 326 and display subsystem 332 to provide displayable images illustrating emissions zone 320 cross section, emissions zone overall surface, and tomographic images representing radiation dose profile within the emissions zone 320. In a particular embodiment, processor 328 has at least one processor as known in the art of computing and a memory system containing machine readable instructions for processing multiple sets of images to construct the three-dimensional models of light emissions in the emission zone 320, and to prepare displayable images representing radiation dose profile in the emissions zone; the memory containing machine readable instructions may be the same or a different memory than the memory 326 in which images are stored.

In an embodiment, processor 328 has calibration information in its memory system 326, and translates the determined three dimensional models of Cherenkov light emission in the emissions zone into three dimensional models of radiation intensity and/or dose.

Monte Carlo simulations are used to study the complex directionality of Cherenkov radiation at each spatial location within the irradiated tank. Due to the finite field of view of the cameras, the intrinsic proportionality between the imparted dose and emitted Cherenkov radiation may be distorted. Therefore necessary calibration factors may be sought through analysis of the system and its camera placements. Additional correction factors may be necessary to correct for inherent differences between the emitted Cherenkov light and imparted dose, specifically spatial locations where the relative fluence of low keV energy electrons is high.

In an alternative embodiment particularly suitable for overcoming the directionality of Cherenkov radiation, a fluorophore, fluorescent dye, or phosphor is added to fluid in the tank, or to the material of a solid phantom. This fluorophore, fluorescent dye or phosphor absorbs some energy from the Cherenkov radiation. The fluorophore then isotropically emits part of the absorbed energy as light that is imaged by the cameras, the profile of light emitted by the fluorophore or phosphor is indicative of beam profile. In a particular embodiment, the fluorescent dye fluorescein is used because it absorbs in the blue near peak Cherenkov emissions, emits light of around five hundred nanometers that is easily imaged, and has a very high quantum yield; in other embodiments other fluorescent or phosphorescent materials may be used.

Because fluorescent and phosphorescent emissions are generally omnidirectional, a fluorophore, fluorescent dye, or phosphor in a phantom helps overcome distortions that may otherwise result due to the directionality of emitted Cherenkov radiation, whether the charged particles are part of a charged-particle radiation beam or induced by high-energy photons of a gamma-ray photon beam. Similarly, a phantom may be constructed of a scintillating material in which light is isotropically emitted via phosphorescence from the ionization of the scintillating material itself, as well as directionally via Cherenkov emission from energetic charged particles.

Since high index materials may absorb radiation differently than does tissue, in an embodiment processor 328 has calibration information in its memory system for adjustment for beam attenuation in the phantom, and translates determined three dimensional models of light emission in the emissions zone into three dimensional models of radiation dose in tissue using that calibration information.

While Cherenkov radiation is emitted during beam pulses 206 (FIG. 5), light emitted 209 from fluorophores or phosphors lags the beam and decays exponentially after each pulse of the beam turns off as illustrated. Similarly, some long-persistence scintillating materials have decay time constants on the order of four hundred or more nanoseconds. In an embodiment therefore, an effective shutter interval during beam pulse 206 is used to image light primarily emitted by Cherenkov mechanisms, and an effective fluorescent shutter interval 211 is used to capture light emitted from a phantom containing a photoluminescent material by scintillating, fluorescent and phosphorescent mechanisms. In this embodiment, light imaged by cameras 316, 318 is recorded as image pairs, with a first image of each pair indicative of light emitted during beam pulse 206 and a second image of each pair indicative of light emitted during the fluorescent shutter interval 211. Processor 328 therefore executes machine-readable instructions in associated memory, such as memory 326 to reconstruct beam shape and beam energy distribution profiles from the captured image pairs.

In an alternative embodiment, cameras 316, 318 use a single shutter interval overlapping the beam, but are spectrally-sensitive cameras such that fluorescent and Cherenkov emissions can be distinguished in processor 328 by the characteristic color, or wavelengths, of these emissions. At typical beam energies, Cherenkov radiation tends to be blue and material-independent, while photoluminescence has wavelength, or color, that is material-dependent and, for typical materials, is longer in wavelength, or redder, than Cherenkov radiation. The spectrally-sensitive cameras may have color-matrix filters on their photosensor as is common for color electronic cameras, may be a combination of a filter-changing device, such as a rotating filter wheel, or another form of spectrally-sensitive camera. In a particular embodiment, a first image is taken using a spectral zone, such as in the blue, where no scintillation or fluorescent emissions exist, but where Cherenkov radiation is expected, and a second image at another wavelength where fluorescent emissions or scintillation do exist. The intensity of the first image is adjusted to extrapolate the intensity contribution of Cherenkov radiation to the second spectral image based on the known inverse square intensity dependence of Cherenkov and electrooptical system characteristics, then the adjusted image is subtracted from the second image to provide a third image, the third image being a corrected, unmixed, image of fluorescent emissions. In this embodiment, the third image from each of several angles is used to determine beam profile in the phantom.

In an alternative embodiment, in order to increase sensitivity and improve contrast, images obtained during and after 211 multiple pulses 206 of the beam are summed or averaged.

In an alternative embodiment, low intensity non-time-varying illumination is used in the environment. In order to image both Cherenkov and fluorescent radiation, images are captured in threes, in each three one image, a background image, is captured prior to, or long after, beam pulse 206, a second image during beam pulse 206, and a third image immediately after 211 the beam pulse 206 and during the fluorescence decay time. In an alternative embodiment, the background image is captured well after the third image. In order to increase sensitivity and improve contrast, image threes are obtained surrounding multiple pulses 206 of the beam, these are then averaged. To determine fluorescent emissions, the processor subtracts the averaged background image from the averaged third image after 211. Similarly, to determine the sum of partial fluorescent emissions and Cherenkov radiation, the averaged background image is subtracted from the averaged second image acquired during the beam pulse 206.

In alternative embodiments where a fluorescent additive is not used, or where only fluorescent emissions during decay time are imaged, image pairs are captured, with a background image captured before or well after the beam pulse, and a data image during, or during the decay time after, the beam pulse. Averaged background images are subtracted from averaged data images to provide a corrected data image.

In an embodiment, an operator may turn on the beam, and have the system construct a model of emissions zone 320, then turn off the beam and view the images provided on display subsystem 332. If the beam fails to meet specifications 714 for a particular treatment, the operator may then use the images provided on display subsystem 332 to determine a different setting of beam-shaping apparatus 314 that should provide a beam that more closely resembles a beam desired for treatment of a patient. The operator may then adjust beam shaping apparatus 314, following which the beam is turned back on while new images of Cherenkov radiation in emissions zone 320 captured by the cameras 316, 318, 370, 374, the beam then being turned off and a new three-dimensional model of the emissions zone and displayable images prepared. Once beam profile meets a desired beam profile, the phantom is removed and replaced by a patient, and the system may then be used to provide radiation of the desired profile for treating the patient.

In an embodiment, parameters of the three dimensional model of the emissions zone and the displayable images are recorded in a machine-readable memory system, such that the model and images may be used to document treatment, for periodic quality assurance and calibration, or to seek regulatory approvals. In another embodiment, the parameters of the three dimensional model are used to satisfy monthly or other periodic quality assurances checks on the clinical electron and x-ray photon beam qualities.

In an embodiment, the system is utilized with optically translucent anthropomorphic tissue phantoms, or complex tissue phantoms to capture images of the beam shape in more complex geometries and tissue compositions than is possible in homogeneous water phantoms.

For purposes of this document, photoluminescent materials include fluorophores, or fluorescent materials, phosphors, or phosphorescent materials, and scintillation crystals. Generally, photoluminescent materials respond to absorbed radiation by entering an excited state, and emit light at a material-dependent wavelength after a decay time of the excited state.

Combinations.

A system for providing and monitoring radiation therapy designated A has a source of high energy radiation disposed to provide a radiation beam to a treatment zone; apparatus for preventing interference by room lighting; apparatus for collecting light from the treatment zone; a detector for detecting the collected light; a processor adapted to determine an oxygenation of tissue within a subject in the treatment zone from detected light.

A system designated AA incorporating the system designated A wherein the high energy radiation has a charged-particle or photon energy exceeding 6 MeV.

A system designated AB incorporating the system designated AA wherein the detector is adapted to perform spectral analysis of light, and where the processor is adapted to determine a metabolic activity of tissue within the subject from spectral analysis of light collected from the subject.

A system designated AC incorporating the system designated AA or AB wherein the processor is adapted to determine a metabolic activity of tissue from fluorescent light emitted within the subject, the fluorescent light emitted upon stimulation by Cherenkov radiation.

A system designated AD incorporating the system designated A, AA, AB, or AC wherein the fluorescent light is emitted from photoluminescent materials or fluorophores induced in the tissue by prior administration of a biochemical compound to the subject which localizes in tumor tissues of the subject.

A system designated AE incorporating the system designated A, AA, AB, AC, or AD wherein the apparatus for by preventing interference by room lighting comprises timing interfaces adapted to determine timing of pulses of the source of high energy radiation and to synchronize light capture by the apparatus for collecting light emitted from the subject.

A system designated AF incorporating the system designated AE wherein the timing interfaces configure the detector to detect light during at least one beam pulse as detected light during the beam, and light immediately following the at least one beam pulse as detected fluorescent light, and the processor is configured to determine Cherenkov light from the detected light during the beam and detected fluorescent light.

A system designated AG incorporating the system designated A, AB, AC, AD, AE, or AF wherein the detector is adapted to spectrally analyze the collected light.

A system designated AH incorporating the system designated A, AB, AC, AD, AE, or AF wherein the detector comprises an array photosensor of a camera.

A system designated AJ incorporating the system designated A, AB, AC, AD, AE, AF, or AH wherein the apparatus for collecting light comprises optical fibers and the detector is a multichannel spectrographic detector.

A system designated AK incorporating the system designated A, AB, AC, AD, or AE wherein the apparatus for preventing interference includes an enclosure adapted to surround at least a portion of a subject.

A system designated AL incorporating the system designated A, AB, AC, AD, AE, AF, AG, AH, AI, AJ, or AK wherein the light emitted from the treatment zone comprises Cherenkov radiation emitted along a path of the high energy radiation within a subject or phantom in the treatment zone.

A system designated AM incorporating the system designated A, AB, AC, AD, AE, AF, AG, AH, AI, AJ, AK, or AL wherein the detector comprises an array photosensor of at least one camera and the system further comprises a tissue phantom containing a substantially transparent or translucent material and positionable in the treatment zone; the at least one cameras is adapted to image the phantom from a plurality of angles; and an image processing system comprising apparatus for receiving images from the camera, at least one processor, and a memory comprising machine readable instructions for processing the images from the one or more cameras to construct a tomographic three-dimensional model of the emissions zone.

A method of monitoring radiation therapy of a subject designated B having steps of providing a beam of high energy radiation for radiation therapy, the high energy radiation of at least 6 MeV; collecting light emitted from the subject, the light emitted as Cherenkov radiation generated along the beam; spectrally analyzing the collected light; and determining an oxygenation of tissue within the subject from the spectral analysis of light collected from the subject.

A method designated BA including the method designated B further comprising determining a metabolic activity of tissue within the subject from the spectral analysis of fluorescent light collected from the subject, the fluorescent light emitted in consequence of absorption of Cherenkov radiation within the subject.

A method designated BB including the method designated B or BA further comprising administering a fluorescence-enhancing agent to the subject.

A method designated BC including the method designated BB wherein the fluorescence-enhancing agent is 5 aminolevulinic acid (5-ALA) administered to the subject, and wherein at least some fluorescent light is emitted by protoporphyrin IX within the tissue generated by metabolism of 5-ALA.

A method designated BD including the method designated BB wherein the fluorescence-enhancing agent is a fluorophore-tagged antibody.

A method designated BE including the method designated B, BA, or BB wherein the metabolic activity of tissue is determined from fluorescent light emitted by protoporphyrin IX within the tissue.

A method designated BF including the method designated BE further comprising administering 5 aminolevulinic acid (5-ALA) to the subject, and wherein at least some of the protoporphyrin IX within the tissue is generated by metabolism of 5-ALA.

A system designated C for providing a radiation beam for radiation therapy having ability to document radiation beam profile comprising: a tissue phantom containing a substantially transparent or translucent material positionable in the treatment zone and having an index of refraction greater than that of vacuum; a source of high energy radiation capable of providing a beam of radiation, the radiation having sufficient energy to induce Cherenkov radiation in the phantom; one or more cameras positioned to image an emissions zone in an intersection of the beam and the phantom; the one or more cameras adapted to capture a plurality of images of the emissions zone from a plurality of angles; and an image processing system comprising apparatus for receiving images from the one or more cameras, at least one processor, and a memory comprising machine readable instructions for processing the images from the one or more cameras to construct a tomographic three-dimensional model of the emissions zone.

A system designated CA incorporating the system designated C wherein the system is configured to integrate light over a plurality of pulses of the beam for each image.

A system designated CB incorporating the system designated C or CA wherein the phantom comprises a fluorescent material.

A system designated CC incorporating the system designated C, CA, or CB further comprising a timing interface adapted to synchronize the cameras to pulses of the radiation beam.

While the invention has been particularly shown and described with reference to a preferred embodiment thereof, it will be understood by those skilled in the art that various other changes in the form and details may be made without departing from the spirit and scope of the invention. It is to be understood that various changes may be made in adapting the invention to different embodiments without departing from the broader inventive concepts disclosed herein and comprehended by the claims that follow.

What is claimed is:

1. A system for providing and monitoring radiation therapy comprising:
a radiation treatment machine adapted to provide high energy radiation and disposed to provide a pulsed radiation beam having a direction and shape configured to provide radiation treatment to a subject in a treatment zone, the radiation treatment machine external to the treatment zone;
a camera adapted to image the subject in combined ambient light and Cherenkov light generated by interaction of the radiation beam with the subject and emitted from the subject in the treatment zone to form a Cherenkov image;
a processor;
timing interfaces adapted to synchronize imaging of light emitted from the subject to during pulses of the high energy radiation emitted by the radiation treatment machine; and
firmware in the processor adapted to subtract a background image from the Cherenkov image, the background image being an image of the subject in ambient room lighting captured by the camera between pulses of the high energy radiation.

2. The system of claim 1 wherein the timing interfaces configure the camera to detect light during at least one beam pulse as the Cherenkov image, and light immediately following the at least one beam pulse as a fluorescent image.

3. The system of claim 2 wherein the camera is adapted to perform spectral analysis of light, and where the processor is adapted to determine a metabolic activity of tissue within the subject from spectral analysis of light collected from the subject.

4. The system of claim 3 wherein the fluorescent light is emitted from fluorophores induced in the tissue by prior administration of a biochemical compound to the subject, the biochemical compound being a compound that localizes in tumor tissues of the subject.

5. The system of claim 2 wherein the fluorescent light is emitted from fluorophores induced in the tissue by prior administration of a biochemical compound to the subject, the biochemical compound being a compound that localizes in tumor tissues of the subject.

6. The system of claim 1 wherein the camera is adapted to perform spectral analysis of light, and where the processor is adapted to determine a metabolic activity of tissue within the subject from spectral analysis of light collected from the subject.

7. The system of claim 1 wherein the processor is adapted to determine a metabolic activity of tissue from fluorescent light emitted within the subject, the fluorescent light emitted upon stimulation by the Cherenkov radiation.

8. The system of claim 7 wherein the fluorescent light is emitted from fluorophores induced in the tissue by prior administration of a biochemical compound to the subject, the biochemical compound being a compound that localizes in tumor tissues of the subject.

9. The system of claim 7 wherein the timing interfaces configure the camera to detect light during at least one beam pulse as the Cherenkov image, and light immediately following the at least one beam pulse as a fluorescent image.

10. The system of claim 8 wherein the camera is adapted to spectrally analyze the collected light.

11. A system for monitoring radiation therapy machines of the type adapted to provide pulsed high energy radiation having a direction and shape configured to provide radiation treatment to a subject in a treatment zone, the radiation treatment machine external to the treatment zone, comprising:
at least one camera adapted to image the subject in ambient and Cherenkov light generated by interaction of the radiation beam with a phantom or subject in the treatment zone and emitted from the phantom in the treatment zone to form a Cherenkov image contaminated by ambient light;
a processor; and
timing interfaces adapted to synchronize imaging of light emitted from the phantom or subject to during the pulses of the high energy radiation emitted by the radiation treatment machine, and firmware in the processor adapted to subtract a background image from the Cherenkov image, wherein the background image is captured by the camera in ambient room lighting between pulses of the high energy radiation.

12. The system of claim 11 wherein the system further comprises:
a tissue phantom containing a transparent or translucent material positioned in the treatment zone;

wherein the at least one camera is adapted to image the phantom in the treatment zone from a plurality of angles, allowing a plurality of views of an emissions zone in the phantom; and an image processing system comprising apparatus for receiving images from the at least one camera, at least one processor, and a memory comprising machine readable instructions for processing the images from the one or more cameras to construct a tomographic three-dimensional model of the emissions zone.

13. A method of monitoring radiation therapy of a subject comprising:

using a radiation treatment machine to provide a beam of pulses of high energy radiation for radiation therapy;

imaging light emitted from the subject to form a Cherenkov image, the light being Cherenkov radiation generated within an emissions zone along the beam in the treatment zone as the beam intersects tissue of the subject, the imaging light emitted from the subject to form a Cherenkov image being synchronized to and performed during the pulses of high energy radiation;

obtaining a background image of the subject in ambient light, the obtaining a background image of the subject in ambient light being performed between the pulses of high energy radiation;

correcting the Cherenkov image by subtracting the background image;

determining a three dimensional model of the emissions zone within the subject.

14. The method of claim 13 further comprising determining a metabolic activity of tissue within the subject from the spectral analysis of fluorescent light collected from the subject, the fluorescent light emitted in consequence of absorption of Cherenkov radiation within the subject.

15. The method of claim 14 wherein the metabolic activity of tissue is determined from fluorescent light emitted by protoporphyrin IX within the tissue.

16. The method of claim 15 further comprising administering 5 aminolevulinic acid (5-ALA) to the subject, and wherein at least some of the protoporphyrin IX within the tissue is generated by metabolism of 5-ALA.

17. The method of claim 14 further comprising using a timing interface to pulse room lighting on when the beam is off, and for synchronizing the collecting of light to pulses of the beam.

18. The system of claim 1 wherein the system is configured to integrate light over a plurality of pulses of the beam for each Cherenkov image.

19. The system of claim 1 wherein the processor is configured to sum or average Cherenkov light acquired over a plurality of pulses of the beam prior to subtracting the background image from the Cherenkov image.

20. The system of claim 11 wherein the processor is configured to sum or average Cherenkov light acquired over a plurality of pulses of the beam prior to subtracting the background image from the Cherenkov image.

* * * * *